United States Patent [19]

Treatch et al.

[11] Patent Number: 5,007,429

[45] Date of Patent: Apr. 16, 1991

[54] INTERFACE USING 12-DIGIT KEYPAD FOR PROGRAMMING PARAMETERS IN AMBULATORY BLOOD PRESSURE MONITOR

[75] Inventors: James E. Treatch, Phoenix; James R. Mikesell, Scottsdale, both of Ariz.

[73] Assignee: PulseTrend, Inc., Phoenix, Ariz.

[21] Appl. No.: 336,244

[22] Filed: Apr. 11, 1989

Related U.S. Application Data

[63] Continuation-in-part of Ser. No. 98,550, Aug. 21, 1987, Pat. No. 4,830,018.

[51] Int. Cl.$^5$ .............................................. A61B 5/022
[52] U.S. Cl. ................................... 128/677; 364/413.03
[58] Field of Search ................ 128/672, 677, 680–683, 128/687–690, 903–904, 670–671, 700, 706–707, 684–686; 364/413.03

[56] References Cited

U.S. PATENT DOCUMENTS

| | | | |
|---|---|---|---|
| 4,296,756 | 10/1981 | Dunning et al. | 128/904 X |
| 4,531,527 | 7/1985 | Reinhold et al. | 128/903 X |
| 4,550,370 | 10/1985 | Baker | 128/904 X |
| 4,770,189 | 9/1988 | Shyu | 128/903 X |
| 4,830,018 | 5/1989 | Treatch | 128/904 X |

*Primary Examiner*—William E. Kamm
*Attorney, Agent, or Firm*—Kinney & Lange

[57] ABSTRACT

A user interface for directing the programming of operating parameters for patient blood pressure testing into and downloading blood pressure data from ambulatory patient blood pressure monitoring units. The user interface operates on a system comprising a plurality of microprocessor based, ambulatory blood pressure measuring patient units, an office control unit, and a data processing center, typically accessed over telephone lines. An office control unit is used to program patient units with test regimens for specific patients. The control units are also used to download data from the patient units and to transfer the data, along with patient identifying data, to the central data processing facility. The office control unit includes local memory which stores various interface routines, a microprocessor for executing the routines, a 12-character keypad allowing input of integers and a display for displaying prompts to the user. Upon initial power up of the control unit, an operator using the control unit is prompted through a start up sequence and a menu selection sequence to carry out the desired functions of the system. All selections are made, and all operating parameters are entered, through a telephone like keypad. The display indicates to the user which parameter entry of which is called for and which menu items are available for selection. During transfer of data to the central processing facility, additional prompts may be given to the operator by voice over the telephone handset.

4 Claims, 14 Drawing Sheets

INTERFACE USING 12-DIGIT KEYPAD FOR PROGRAMMING PARAMETERS IN AMBULATORY BLOOD PRESSURE MONITOR

CROSS-REFERENCE TO RELATED APPLICATION

This application is a continuation in part of U.S. patent application Ser. No. 07/098,550 filed 21 August 1987, and now U.S. Pat. No. 4,830,018.

BACKGROUND OF THE INVENTION

The invention relates to operation of an interface between a human programmer and a programming controller for ambulatory blood pressure monitoring units, and, more particularly, to operation of an interface utilizing a conventional 12-digit telephone keypad and a prompt display.

Microprocessor controllers are known for the portability they lend to electronic devices and for their low power consumption. As a result of these advantages, microprocessors have been applied to the control many types of devices, including devices intended for the monitoring of human physiological conditions. In the field of medicine, the small size and low power consumption of microprocessors has created the possibility of extended duration monitoring of ambulatory patients by use of portable devices. Acceptance by physicians and patients of these portable devices depends in part upon their simplicity of use.

The manufacturer can, to some extent, anticipate the demands on a portable blood pressure measuring device. It can preprogram an ambulatory patient unit incorporating a microprocessor to execute blood pressure measurements on a periodic basis and to tag the results for storage in memory until opportunity comes for downloading of the information. However, in so doing much of the flexibility that intelligent control affords is lost. Allowing the medical practitioner, or her/his assisting staff, to program intelligent ambulatory diagnostic equipment can only enhance the value of the equipment, provided that programming does not require extensive training, or create the possibility of error in execution of the basic function of the equipment.

SUMMARY OF THE INVENTION

The present invention provides a simplified interface for programming operating parameters into an ambulatory patient blood pressure monitoring unit. It further provides a simplified interface for the downloading of data from the ambulatory blood pressure monitoring unit to a centralized blood pressure data collection data processing facility. The user/system interface operates on a system comprising a plurality of microprocessor based, ambulatory blood pressure measuring patient units, an office control unit, and the data processing center, typically accessed over telephone lines by the office control unit. While described with reference to a system for collecting blood pressure data, the interface of the present invention is applicable to a variety of process monitoring systems, particularly where process monitors are portable and subject to detachment from the control unit during use for monitoring.

The patient units are portable units designed to be worn by a patient during normal daily activities. The patient unit takes blood pressure readings pursuant to a regimen programmed into the patient unit. The patient unit stores the readings in resident memory for later downloading to the data processing facility. The patient units are adapted to accept programming of operating parameters controlling various aspects of unit operation from the office control unit and to transfer blood pressure measurements to the control unit upon interrogation of the patient unit. The office control units transfer blood pressure data, tagged with patient identifying data, to a data processing center, which generates comprehensive medical reports for specific patients, correlated to the patient's peer group.

The office control unit operates in conjunction with a base telephone unit when used for transmission of data to the central data processing facility. The office control unit includes local memory which stores various interface routines, a microprocessor for executing the routines, a 12-character keypad allowing input of integers and a display for displaying prompts to the user. Data communication is provided between the control unit and a selected patient monitor unit by a serial data communication link between the units. For transfer of data to the central data processing facility, a selected patient unit is connected to the office control unit and the office control unit is connected to a telephone set. This permits the central processing facility to transmit additional audio prompts to the user over the telephone handset.

Upon initial power up of the control unit, an operator using the control unit is prompted through a start up sequence and a menu selection sequence to carry out desired on functions of the system. All selections are made, and all operating parameters are entered, through a telephone like keypad. The display indicates to the user which parameter entry is called for and which menu items are available for selection. During transfer of data to the central processing facility, additional prompts may be given to the operator by voice over the telephone handset.

DESCRIPTION OF THE PREFERRED EMBODIMENT

Figure 1:
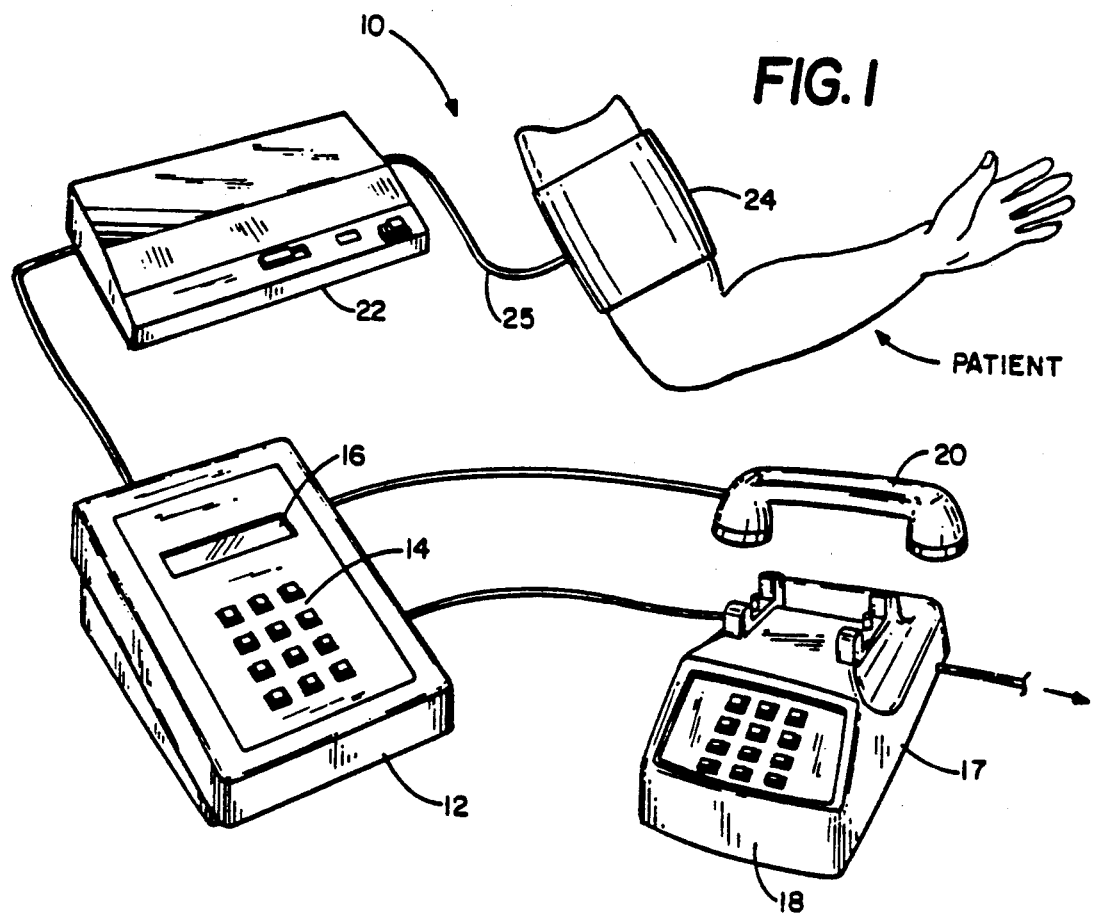
FIG. 1 is a view of the portion of the system located in a physician's office.

FIG. 1 illustrates that portion of an ambulatory patient blood pressure monitoring system 10 located in a medical practitioner's office. System 10 includes a control unit 12 having a 12-character telephone like keypad 14 for the entry of data, selection of operating parameters and the selection of menu options. Control unit 12 further includes a 16 character liquid crystal display 16 for providing visual prompts. Control unit 12 is powered by connection to a conventional wall socket by a cord set (not shown).

Control unit 12 is connected to a conventional telephone 17 through the handset outlet jack of standard telephone base unit 18. Telephone handset 20 of telephone 17 is in turn connected to a handset outlet jack in control unit 12. Telephone 17 is connected to a telephone central switching office (not shown) and can be used conventionally.

Control unit 12 is also connected to an ambulatory patient blood pressure monitor unit 22, which is shown with an arm cuff 24. Patient unit 22 executes periodic checking of the wearer's blood pressure, in accordance with a schedule programmed into the device through controller 12.

Figure 2:
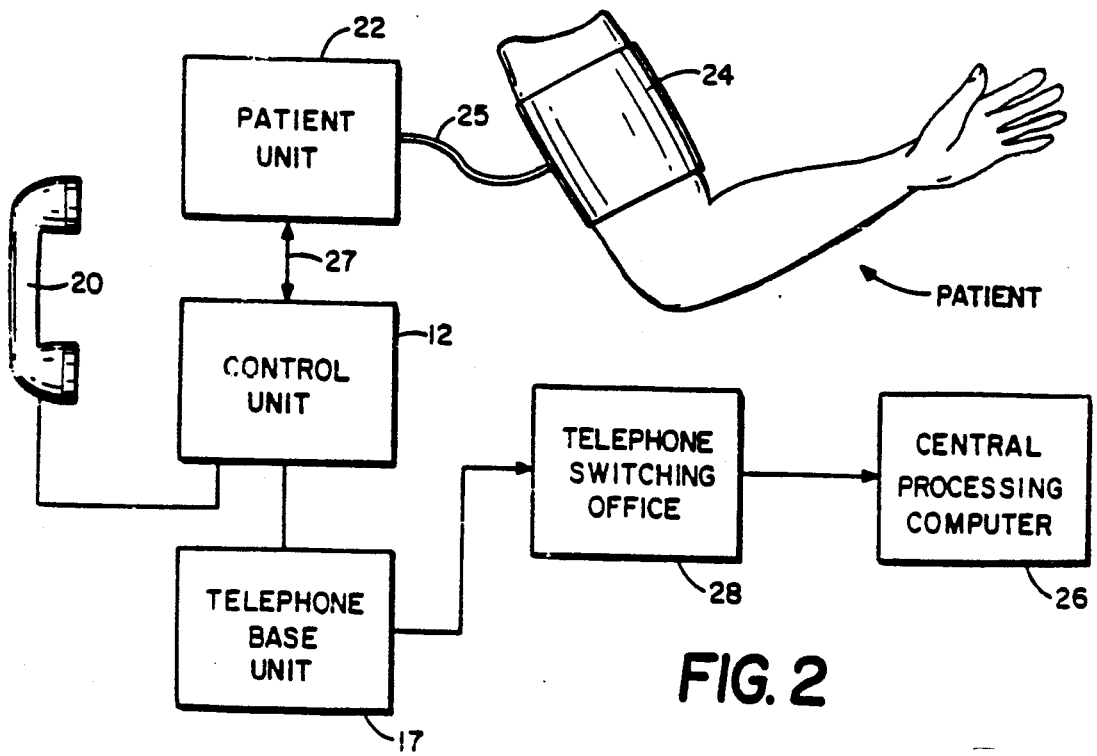
FIG. 2 is a block diagram of an ambulatory patient blood pressure monitoring and reporting system.

FIG. 2 illustrates blood pressure monitoring system 10 in block diagram form. Cuff 24 is placed around a patient's arm and inflated by a pump in patient unit 22 through an air pressure line 25 to determine blood pressure levels. A transducer in patient unit 22 determines the pressure readings on air pressure line 25 including oscillometric variations in pressure due to Korotkoff sounds for determining blood pressure.

Patient unit 22 is detachably connected to control unit 12 via bi-directional serial data link 27. Programming of operating parameters in patient unit 22 is carried out through control unit 12 and downloading of blood pressure data relating to individual blood pressure measurements and time correlation data for each measurement is carried out over bi-directional data link 27.

Control unit 12 is connected to telephone 17 through the handset jack port on telephone base unit 18 and by its own handset jack port to telephone handset 20. Telephone base unit 17 can be connected by a conventional telephone channel through the telephone central switching office 28 to a central data processing facility 26. Data processing facility 26 can provide voice prompts to a user over telephone handset 20 to assist downloading of blood pressure data.

Figure 3:
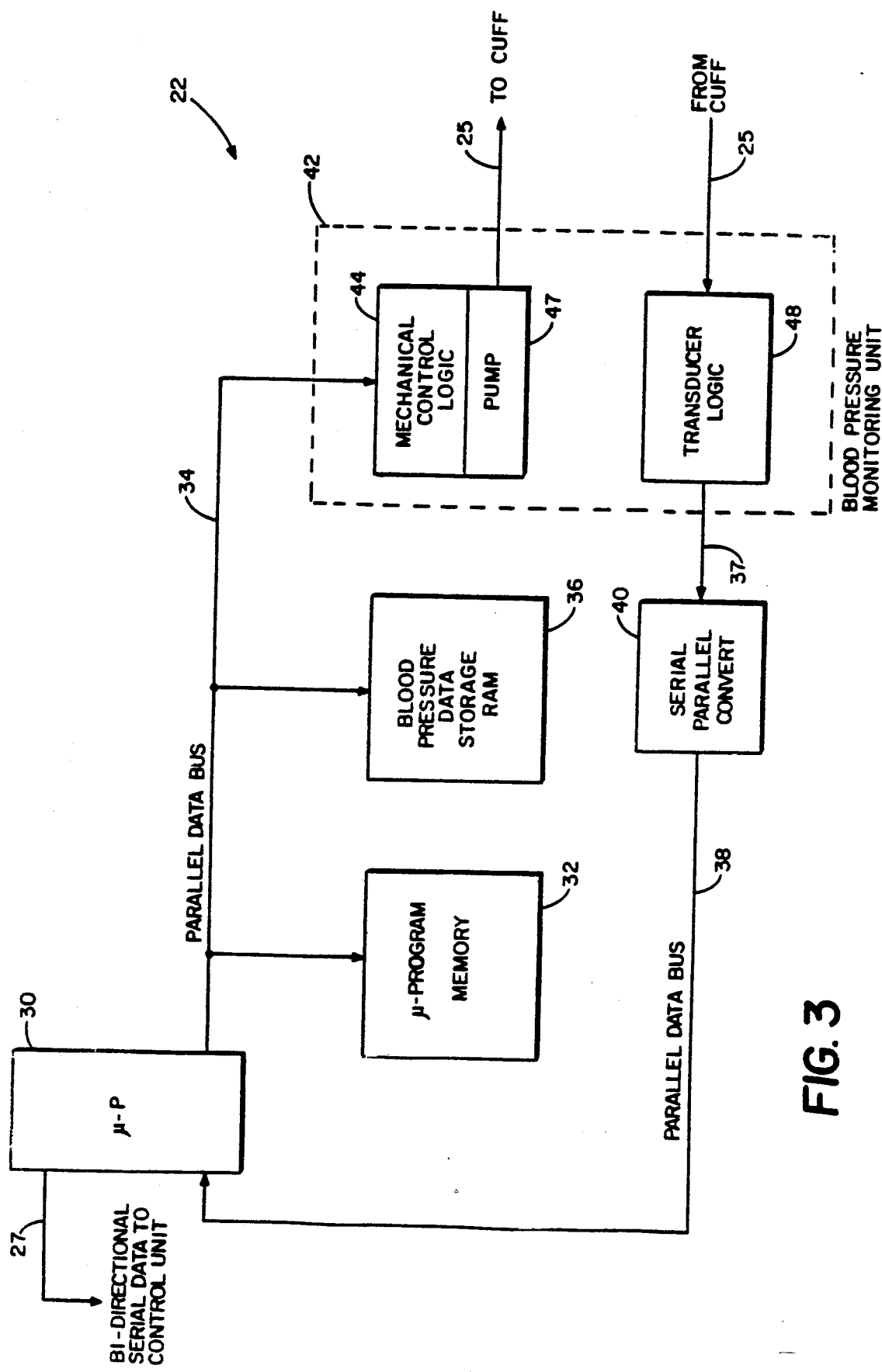
FIG. 3 is a more detailed block diagram of a patient unit.

FIG. 3 illustrates in greater detail an ambulatory patient blood pressure monitoring unit 22. Microprocessor 30 executes routines stored in program memory 32, which the microprocessor accesses over parallel data bus 34. The routines include a real time clock routine for tagging individual blood pressure measurements and a scheduling routine for triggering blood pressure measurements. The routines operate on operating parameters stored at predetermined locations in data storage RAM 36. The operating parameters include the current time (which the monitor itself updates based upon a starting time loaded therein), a time interval between tests during the patient's waking period, a time interval between tests in the patient's sleeping period and the patient's anticipated bed and wake up times. The operating parameters are loaded into storage RAM 36 from bi-directional data link 27 through microprocessor 30 onto parallel data bus 34. Blood pressure data is also stored in predetermined locations in RAM 36 by microprocessor 30.

Ambulatory patient blood pressure monitoring unit 22 includes a blood pressure test unit 42. Microprocessor 30 is connected with blood pressure test unit 42 via a serial to parallel converter 40 over parallel data bus 38 and directly to mechanical control logic 44 over data bus 34. Mechanical control logic 44 initiates operation of a pump 47 for pressurizing the arm cuff over air pressure line 25. Transducer logic 48 is coupled to air pressure line 25 for indicating air pressure therein, including variations in air pressure associated with Korotkoff sounds. Microprocessor 30 executes the clock routine and test regimen routine thereby manipulating the mechanical control logic to control cuff 24 and to record the pressure at which Korotkoff sounds are detected during blood pressure checks.

Air pressure line 25, which connects blood pressure test unit 42 with cuff 24, is used both for inflating the cuff and carrying sound waves related to the presence of Korotkoff sounds to transducer logic 48. Transducer logic 48 operates on pressure readings and oscillometric variations in pressure on link 42 to generate a stream of serial data, converted to parallel data by converter 40, representing blood pressure data. Microprocessor 30 receives this data via parallel data bus 38 and stores this data in RAM 36 via parallel data bus 34, tagged with the date and time that the reading was taken.

Figure 4:
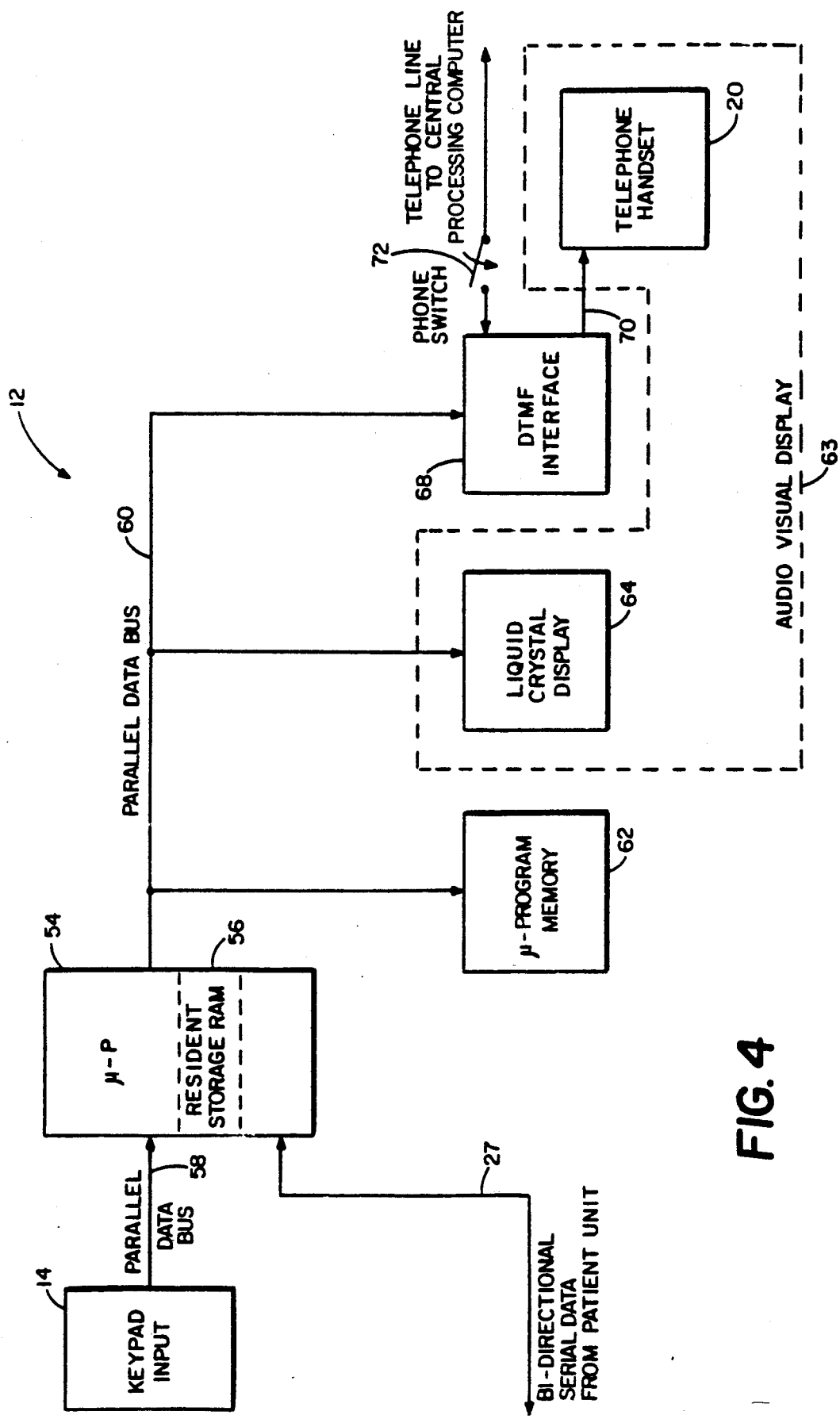
FIG. 4 is a more detailed block diagram of a control unit.

FIG. 4 illustrates in block diagram an office control unit 12 for programming patient units and downloading and transferring data from patient units to a central data processing facility. Office control unit 12 is controlled by microprocessor 54. Microprocessor 54 contains resident storage RAM 56, which is used to store data awaiting transmission to central data processing facility 26.

Microprocessor 54 is connected to keypad 14 by a parallel data bus 58 and to a selected patient unit 22 by bi-directional serial data link 27. Microprocessor 54 accesses control unit operating and interface programs stored in program memory 62 over a parallel data bus 60. Parallel data bus 60 also provides a communication link between microprocessor 54 and a liquid crystal display 64 in audio visual display 63, and a communication link between the microprocessor and a dual tone multiple frequency ("DTMF") interface 68. DTMF interface 68 transmits DTMF signals to telephone 17 for transmission to central switching office 28 for providing switching information to establish a telephone channel and for transmitting data to central data processing facility 26. DTMF interface 68 also passes audio prompts received on telephone link 28 to telephone handset 20 by connection 70. Phone switch 72 is closed by lifting telephone handset 20 from its cradle on telephone 17, thereby allowing transmission of DTMF signals.

Keypad 14 is used by the medical practitioner to input parameters of a test regimen for a particular patient into a selected patient unit 22. Microprocessor 54 then transmits the test regimen information via bidirectional data link 27 to patient unit 22 (shown in FIG. 3). Additionally, keypad 14 is used when data are being downloaded from a patient unit 22 for transmission to central data processing facility 26. At such times, input to keypad 14 is used to tag the blood pressure data with patient identifying data such as the physician's account number, his/her telephone number and social security number.

Visual display 63 is used to prompt the user of control unit 12 on how to execute programming of patient units 22 and on how to transmit data to central data processing facility 26. Generally, liquid crystal display 64 carries locally generated prompts and telephone handset 20 carries prompts generated by central data processing facility 26. The prompts indicate a variety of error conditions and direct the user through the proper sequence of steps for execution of the desired procedure.

DTMF interface 68 is connected via a telephone channel through switching office 28 to the central data processing facility. The system user initiates data transmission by selecting the appropriate menu item from control unit 12 and lifting the telephone handset 20 (shown in FIG. 1), closing switch 72. Control unit 12 can then execute a routine for calling the central data processing facility, as explained more fully below. Once a telephone link is established between control unit 12 and the central data processing facility, the blood pressure information, downloaded from patient unit 22 and stored in resident storage RAM 56 in microprocessor 54, is transmitted to the central data processing facility. The information is transmitted in accordance with a protocol suitable for transmission as DTMF signals. DTMF interface 68 receives the signals over data bus 60 and converts the data signals to DTMF signals.

The central data processing facility returns selected prerecorded or computer generated audio messages to the transmitting user indicating additional steps to be taken, acknowledging successful reception of the data, or indicating that the data transmission was not completely received. Audio messages are relayed by DTMF interface 68 to telephone handset 20. Depending upon the message, the user can discontinue the communication link, or reinitiate the data transmission sequence.

The routines provided control unit 12 for generating prompts in their proper order are described below with reference to a series of flow charts. Prompts direct selection of one or a series of characters present on 12 key keypad 14 to enable the user to operate blood pressure measurement system 10. The keys of keypad 14 are the ten digits, the "*" sign and the "#" sign. It will be understood that the control unit executes other routines, not requiring user interaction, without the display of prompts. The routines not directly interacting with the user interface are not described here.

Figure 5:
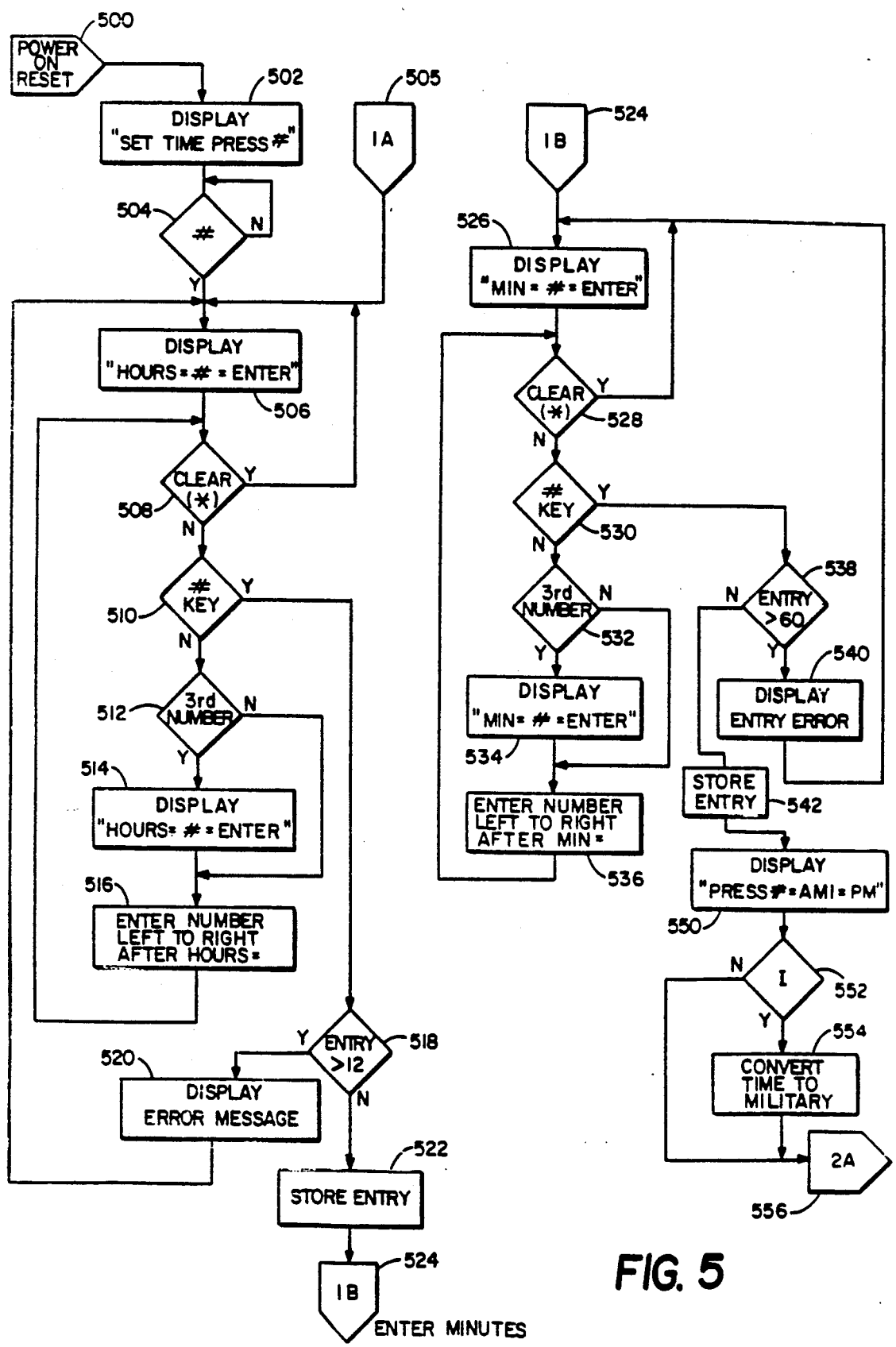
FIG. 5 is a flow chart diagram of the initial power up and time entry routines for an office control unit.
Figure 6:
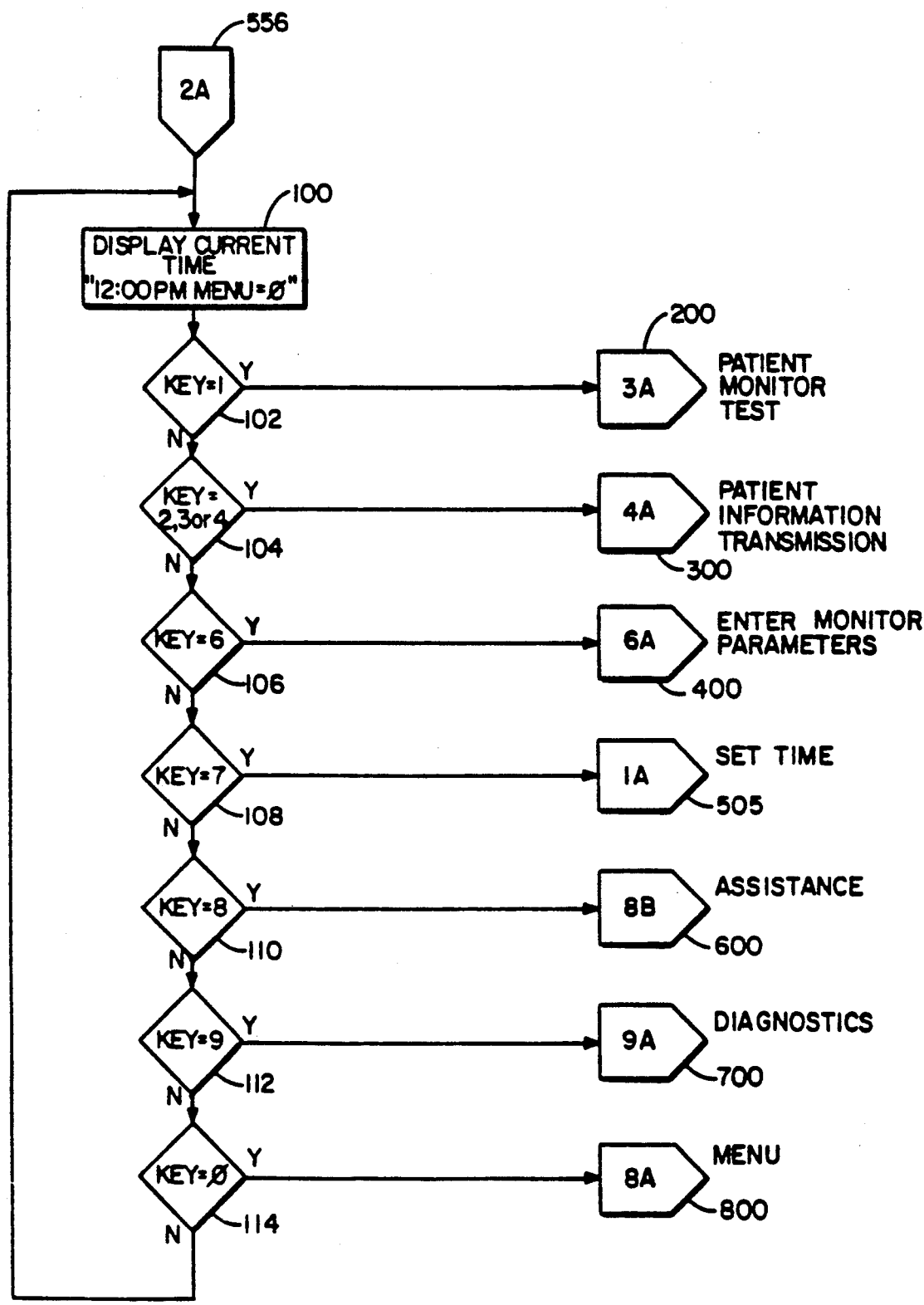
FIG. 6 is a flow chart diagram of the idle loop routine for the control unit awaiting menu selection by a user.

FIG. 5 illustrates a power on, time entry (hereinafter "reset") routine executed automatically by office control unit 12 upon power up. Execution of the reset routine does not require connection of control unit 12 to either a patient unit 22 or to a telephone base unit 17. The reset routine is entered at entry step 500 by control unit 12 automatically upon power up. The reset routine can also be entered at link step 505 upon selection of the "Set Time" option from the menu routine (FIG. 6). The reset routine sets the internal clock of control unit 12. The clock output is automatically transferred to a patient unit 22 as an operating parameter upon programming of a test regimen into the patient unit. Entry to the reset routine from step 500 results in display of the prompt "SET TIME PRESS #" on liquid crystal display 16 at step 502 and entry into an idle loop at step 504. Until the user presses the "#" key on keyboard 14, the message of step 502 continues to be displayed. When the "#" key is detected, or when the reset routine is entered from step 505, the program moves to step 506, which directs display of a new visual prompt "HOURS #=ENTER". This prompt remains present until one of three events occurs, indicated by steps 508, 510 and 512. Should the user press the "*" key, microprocessor 54 clears whatever numerical entry has been made (step 508) and returns to step 506 for display of the hour entry prompt. Should the user enter a digit, microprocessor 54 checks whether the digit is the third one entered (step 512). If the digit is not the third digit entered, microprocessor 54 enters the digit into the display from left to right (step 516). If the digit is the third digit entered, the display is cleared and the hour entry prompt is displayed (step 514). The third digit is then displayed as the first digit of a new entry sequence, again beginning from the left (step 516). From step 516 the program returns to a waiting state ahead of step 508 until entry of another character from the keyboard.

Detection of entry of the "#" key (step 510) indicates attempted entry of the hour portion of current time. Upon attempted entry of the time in hours, microprocessor 54 evaluates the entered time for correspondence to a reasonable value using a 12 hour standard. Accordingly, if the value of the entry exceeds 12 (step 518), an error condition exists, and entry of the value is refused. The routine branches to step 520 and an entry error message is briefly displayed. Thereafter the routine returns to step 506 and recommences the hour entry portion of the reset routine. Where the value is an appropriate value, it is stored to memory (step 522), subject to periodic updating by an internal clock program, and the routine exits to the Enter Minutes (step 524) portion of the reset routine.

The program moves to step 526, which directs display of a new prompt "MIN= #=ENTER". This prompt remains present until one of three events occurs, indicated by steps 528, 530 and 532. Should the user press the "*" key, microprocessor 54 clears whatever numerical entry has been made (step 528) and returns to step 526 for display of the minute entry prompt. Should the user enter a digit, microprocessor 54 checks whether the digit is the third one entered (step 532). If the digit is not the third digit entered, microprocessor 54 enters the digit into the display from left to right (step 536). If the digit is the third digit entered, the display is cleared and the minute entry prompt is displayed (step 534). The third digit is then displayed as the first digit of a new entry sequence, again beginning from the left (step 536). From step 536 the program returns to a waiting state ahead of step 528 until entry of a character from the keyboard.

Detection of entry of the "#" key (step 530) indicates attempted entry of the minute portion of current time. Upon attempted entry of the time in minutes, microprocessor 54 evaluates the entered time for correspondence to a reasonable value using a 60 minute standard. Accordingly, if the value of the entry exceeds 60 (step 538) an error condition exists and entry of the value is refused. The routine branches to step 540 and an entry error message is briefly displayed. Thereafter the routine returns to step 526 and recommences the minute entry portion of the reset routine. Where the value is an appropriate value, it is stored to memory (step 542), subject to periodic updating by an internal clock program, and the routine exits to the military time conversion portion of the reset routine.

After step 542 the microprocessor causes the display of the message "PRESS #=AM 1=PM" (step 550). Because the clock routine operates on a 24 hour basis, P.M. entries are converted in memory to a 24 hour standard. Accordingly, if a PM entry is detected (step 552) the hours in memory are converted to military time (step 554). Thereafter the A.M. and P.M. paths merge at link step 556 which is the entry point to the menu selection idle routine.

The idle/menu selection routine is illustrated in FIG. 6. From entry point step 556 the routine immediately enters step 100 and displays the prompt message "HH.MM TM MENU=0", where HH is hours, MM is minutes and TM indicates the position of the AM/PM indication. After display of the prompt the microprocessor idles, scanning keyboard 14 for a keyed entry, indicating selection of a menu item. An entry of a "1", determined in the routine at step 102, pushes the microprocessor into execution of a Patient Monitor test routine entered at link step 200. An entry of a "2, 3 or 4", detected at step 104, initiates execution of a data transmission routine entered at link step 300. Entry of a "5" breaks a telephone link established during a data transmission routine, but has no effect on idle/menu selection operation. Entry of a "6", detected at step 106, initiates a patient monitor programming sequence entered at step 400. Entry of a "7", detected at step 108, results in initiation of a control unit reset routine entered at step 505. An "8", detected at step 110, initiates an assistance routine entered through step 600. Entry of a "9", detected at step 112, results in execution of a diagnostics routine beginning at step 700 used in maintenance of the equipment. Entry of a "0", detected at step 114, results in a routine being executed beginning with step 800 for scrolling through the menu. The function of each routine, except the already described reset routine, is explained more fully below.

Figure 7:
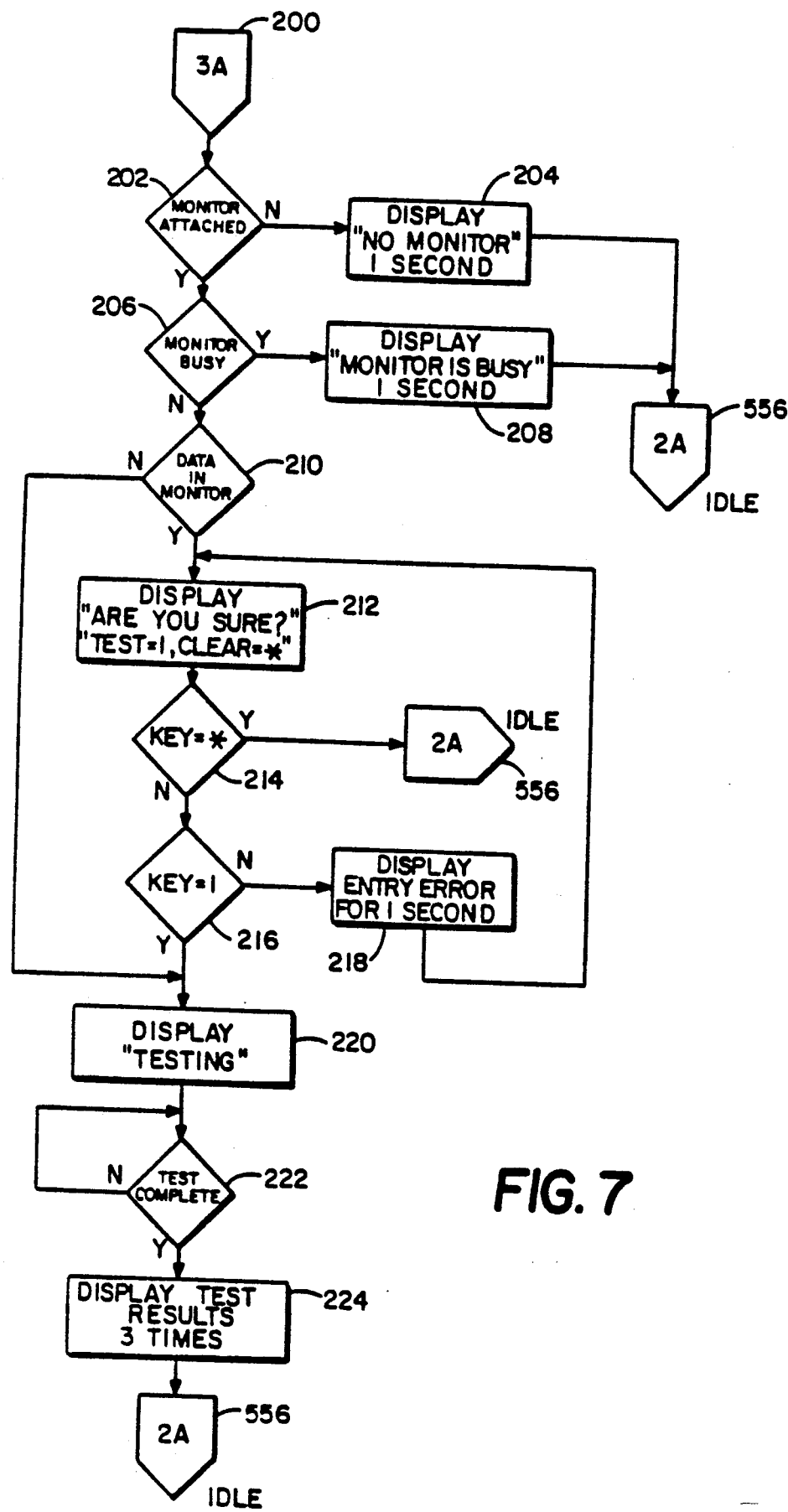
FIG. 7 is a flow chart diagram of the start test routine.

FIG. 7 illustrates the test routine. The test routine is not described in detail save in its relation to the user interface function of the control unit. Patient monitor test routine is entered at step 200. At step 202 them microprocessor determines if it is linked to a patient monitor unit. If not, the routine is exited via step 204. The message prompt "NO MONITOR" is displayed for one second and the routine is exited at step 556, returning operation of the control unit to the idle/menu selection routine. Where a patient unit is attached, the microprocessor of the control unit interrogates the patient monitor (step 206) to determine if the test routine can be carried out. Conditions under which it would not be able so to do include the absence of batteries in the patient monitor. If the monitor cannot respond, the routine is exited via step 208 to the idle routine through link step 556 with the prompt "MONITOR IS BUSY" being displayed for one second.

The monitor test routine protects data which may be present in the monitor. At step 210, the control unit interrogates the monitor to determine the presence of data in the monitor memory. The presence of data branches the routine to step 212, which scrolls display of two prompts on the liquid crystal display, the first being "ARE YOU SURE?" and the second being "TEST=1, CLEAR=*". Each prompt is displayed for about 1 second before the control unit alternates prompts. Entry of the "*" key results in the routine being exited at step 214 and program execution being returned to idle through link step 556. Entry of any other character, except "1", results in branching of the program from step 216 to step 218 for display of the prompt of an entry error prompt for 1 second and return of execution to step 212.

Entry of a "1" after display of the prompts of step 212, or the absence of data stored in the monitor, determined at step 210, results in the routine passing to step 220, initiating a testing routine of the patient monitor. During this routine data stored in the monitor is subject to erasure. Microprocessor 54 displays the message "TESTING" to indicate the status of the control unit. Upon completion of the test (step 222) the routine is exited to step 224 indicating display of the test results and the microprocessor exits to the idle state by step 556.

Figure 8:
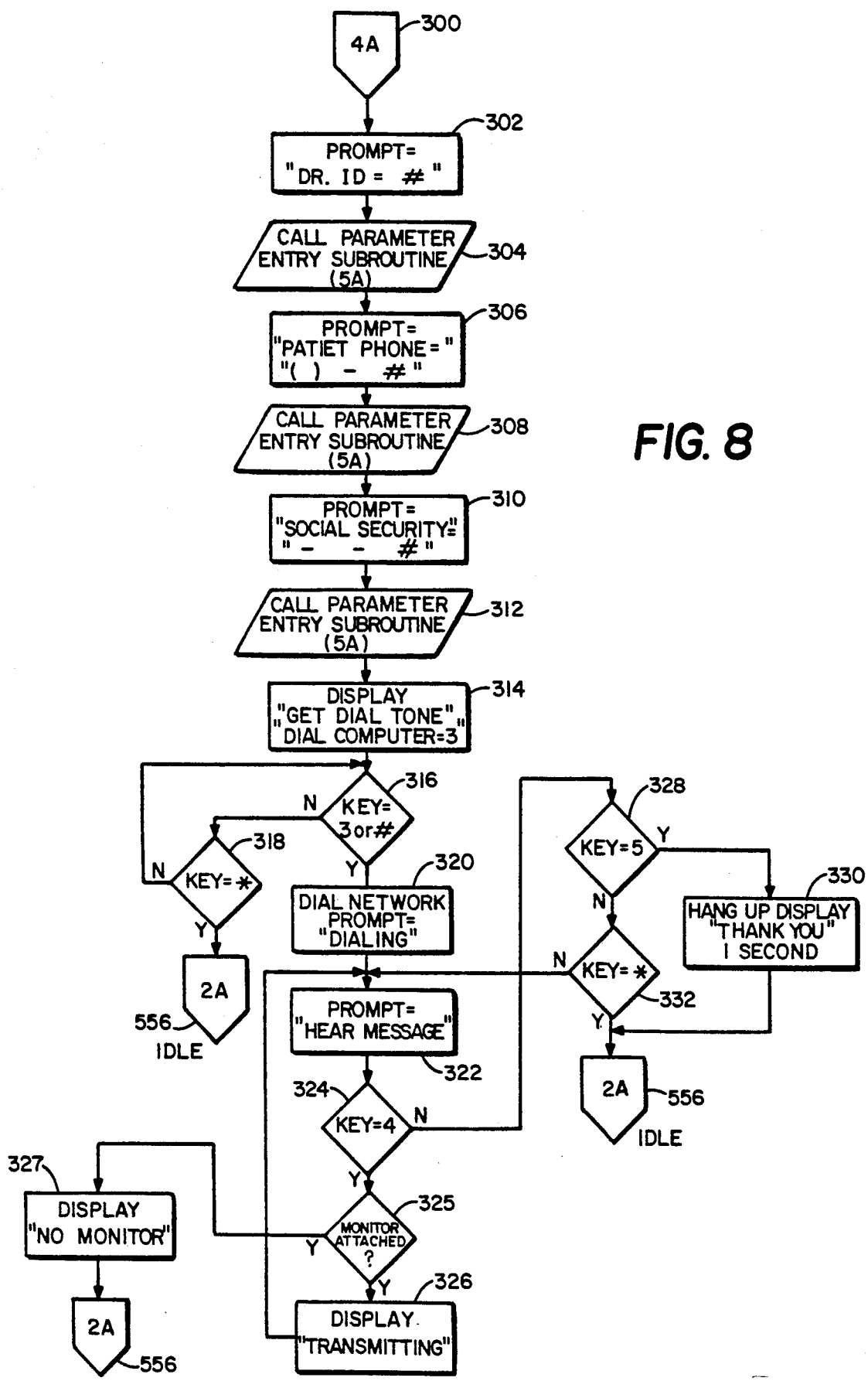
FIG. 8 is a flow chart diagram of patient data entry routine.

FIG. 8 illustrates the sequence of prompts generated by microprocessor 54 on the liquid crystal display of control unit 12 for guiding a user through a data transmission sequence. This routine is used when the control unit is attached both to a patient monitor with data to be downloaded and to a telephone for transmission of the data to the central data processing facility. Entry to the data transmission sequence occurs from the idle/menu selection routine through step 300. Step 302 defines a parameter entry size area and displays the prompt "DR. ID =     #". A parameter entry subroutine (FIG. 11) is then called (step 304) taking as an input variable the size of the area allowed for entry of the desired parameter. Subsequent to entry of the doctor's I.D. number, the prompts "PATIENT PHONE=" and "(   ) -     #" are scrolled (step 306) until the user begins entry of the number. Entry of the first digit of the number results in the parameter entry subroutine being called (step 308) and the display being locking onto the "(X ) -     #" display (where X represents the entered digit) until completion of entry of the phone number as determined within the parameter entry subroutine (step 308). Steps 310 and 312 allow entry of still more specific patient identifying data, herein, by way of example, the patient's social security number. The prompts "   - -     " and "SOCIAL SECURITY=" are scrolled (step 310), and the parameter entry subroutine is called (step 312) upon entry of the first integer.

Thereafter the control unit prompts the user to acquire a telephone link to the central data processing facility (step 314) by scrolling the prompts "GET DIAL TONE" and "DIAL COMPUTER=3". The proper response of the user is to pick up the telephone handset, and after acquisition of a dial tone, to enter a "3" to increment the program to step 316. The control unit will respond to keying of either "3" or "#" (steps 316 and 320) to commence automatic dialing of the central data processing facility. Entry of any other key results in the microprocessor checking to see if the clear key "*" was entered (step 318), in which case the routine is exited and the control unit returns to execution of the idle/menu selection routine by way of link step 556. If a character other than "*, 3, or #" has been entered the control unit ignores the character and continues prompting the user to enter a "3" to begin the dialing sequence.

As noted above, entry of the appropriate character increments the program to step 320, which initiates dialing of the data facility by the control unit. The telephone number of the appropriate data processing facility is stored in the program memory resident storage RAM of microprocessor 54. After dialing is completed microprocessor 54 directs display the prompt "HEAR MESSAGE" (step 322). This prompt indicates to the user to listen to the telephone handset for an audio prompt generated by the central data processing facility. The central data processing facility can generate one of several audio messages. The first audio prompt directs the user to enter a "4" to begin transmission of data. Other audio prompts direct the user to hang up the phone, that a data transmission was garbled, that the link is being broken from the data processing facility and similar types of messages. Entry of a "4" is detected at step 324 resulting in the office control unit interrogating an attached patient monitor unit for blood pressure data, formatting and transmitting the data to the central data processing facility and displaying the message "TRANSMITTING" on the liquid crystal display. If no monitor is attached to the control unit or is in some way disabled (step 325), the routine is exited and program execution is returned to the idle routine (step 327).

After data transmission is successfully completed the control unit returns to the "HEAR MESSAGE" prompt and the central data processing facility directs the user to enter "5" to break the telephone link. If the transmission does not correspond to the format expected, the central data processing facility gives an audio prompt indicating a garbled message and directing the user to repeat the data transmission, if the data still fails to meet expectations the central data processing facility tells the user to hang up and try again later and breaks the connection.

Keying a "5" (step 328) results in termination of the telephone linkage, and the display of the message "THANK YOU" (step 330) before exiting the routine to the idle routine (step 556). Detection of any other key, except "*", simply breaks the connection and returns the control unit to the idle state (steps 332 and 556). A "*" loops the routine back into the data transmission initiation stage of step 322, although it has no effect on the central data processing facility's readiness to accept data if the telephone channel has already been cut.

Figure 9:
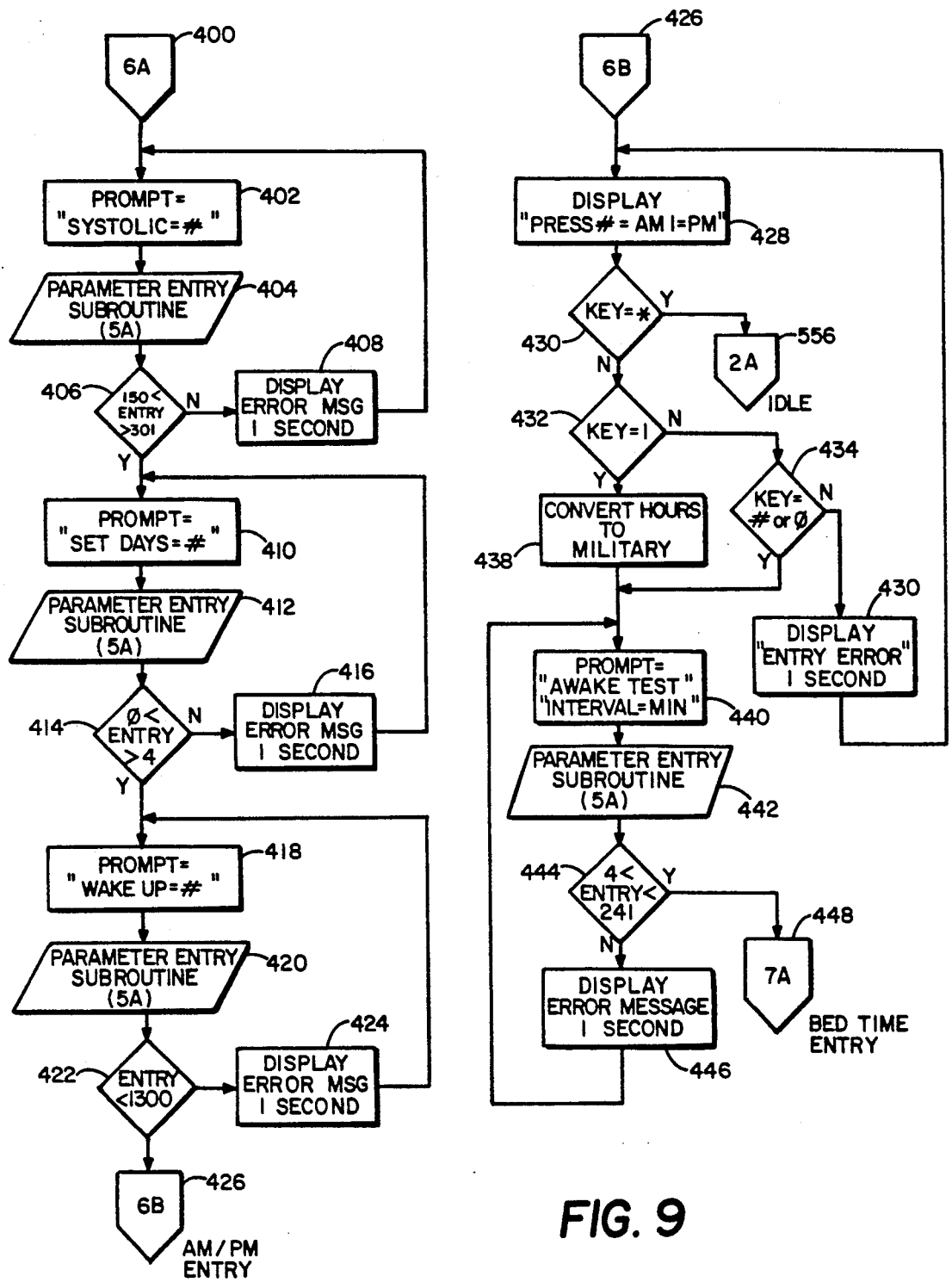
FIG. 9 is a flow chart diagram of a routine for selecting patient monitor parameters.
Figure 10:
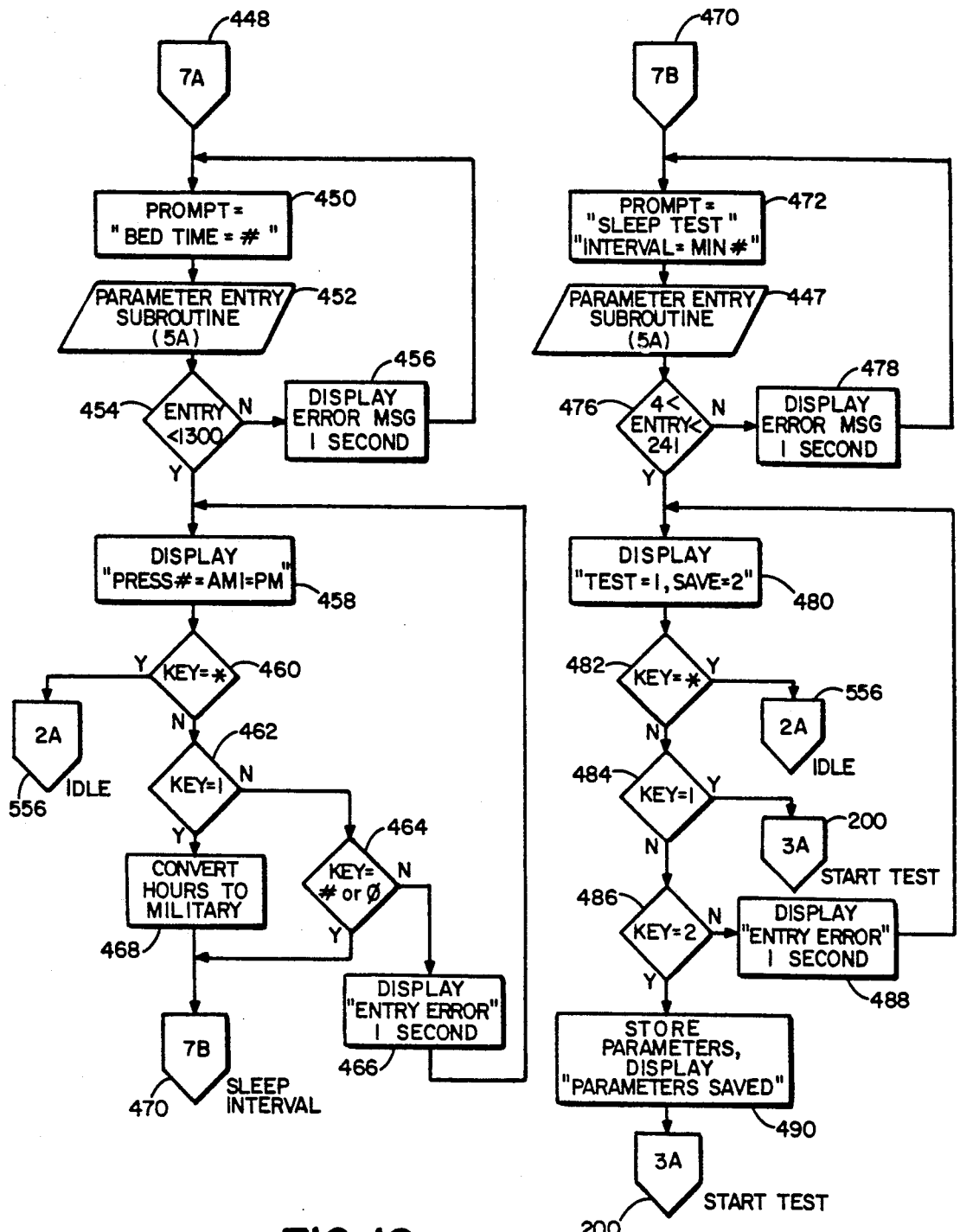
FIG. 10 is a continuation of FIG. 9.

FIGS. 9 and 10 illustrate the prompting sequence generated by control unit 12 and the Enter Parameter routine for directing the programming of operating parameters into a patient monitor unit. As described above, the parameters determine the particulars of the test regimen for the ambulatory patient, while preprogrammed routines determine the general aspects of the test regimen. The enter parameter routine is entered through step link 400. Step 402 directs entry of a blood pressure selected to exceed the patient's maximum probable systolic blood pressure by 30 mm of mercury. The prompt displayed reads "SYSTOLIC= #". Entry of a first integer causes the routine to call the Parameter Entry Subroutine (step 404) for determining the reasonableness of the entry. The Parameter Entry Subroutine is described below with reference to FIG. 11. At step 406 the value of the selected parameter is checked for conformity to upper and lower permitted values, and where the parameter entered fails to conform, the routine returns to the prompt step 402 by way of step 408. Step 408 causes an error message to be briefly displayed.

Conformity of the parameter entered in steps 402 and 404 to the permitted range results in the routine advancing to step 410, wherein the term in days of the test regimen is established. At step 410 the prompt "SET DAYS= #" is displayed. The Parameter Entry subroutine is called at step 412 again resulting in the entries made by the user/programmer being evaluated for reasonableness. At step 414 the selected operating parameter, herein consecutive days of the test regimen, is compared against a maximum of three days and a minimum of one day (step 414). Nonconformity advances the routine to step 416 resulting in an error message prompt display for one second and return of the program to step 410. A conforming entry (1, 2, or 3) causes the program to advance to step 418.

The test regimen allows for a different schedule during sleep periods and waking periods, in part to avoid excessive interruption of the patient's sleep routine. Default settings of a test every 20 minutes during waking periods and 120 minutes during sleeping periods can be varied. The probable sleep and waking periods can also be programmed through appropriate selection of parameters. Step 418 calls for entry of the probable beginning of the waking period of the patient. Entry to the step results in display of the prompt "WAKE UP= #". Entry is to be in accord with a 12 hour clock and accordingly entries must be less than 1300. Again, upon entry of the first digit of the time, the routine calls the parameter entry subroutine (step 420) for determining the conformity of the entry to the number of digits permitted or required. After exiting the subroutine the routine checks the entry at step 422 for conformity to the 12 hour clock standard. Conformity results in the routine passing on to the AM/PM determination (step 426) while error results in the routine branching to step 424, display of an error message and return of the routine to the wake up prompt at step 418.

From step 426 the routine enters a conformity routine for converting the wake period beginning parameter entry to a 24 hour clock standard (step 428). Step 428 directs display of the prompt "PRESS #=AM 1=PM". At steps 430, 432 and 434 the routine scans the keyboard for entry of the pound sign or a "1" as directed, and for the clear sign which results in exit of the routine (by way of steps 430 and 556). A keyed entry of "1" results in conversion of the original parameter to the 24 hour clock (step 438) by addition of 12 hours to the entered parameter. Keying entry of a character other than "1"or "*" results in the routine advancing to step 434. Step 434 determines if the "#" key was entered, in which case the entered time can be saved as entered allowing the routine to skip step 438. Occurrence of an entry other than the "#" key indicates an entry error, resulting in display of an entry error message (step 436) and return of the routine to step 428.

At step 440 the user is prompted to enter a time interval between blood pressure tests for the patient's waking interval. The prompt alternates 1 second displays of "AWAKE TEST" and "INTERVAL=MIN". A default setting may be shown in the INTERVAL prompt such as "20MIN". Entry of the first digit of the interval freezes the prompt on the INTERVAL prompt and displays the digit entered. Entry of the first digit also results in calling the Parameter Entry Subroutine (step 442) for assuring that the entry has the appropriate number of numerical characters. After exiting the Subroutine the interval is checked for conformity to an appropriate duration (step 444) herein a period of between 4 and 241 minutes. If the entry is too short or too long in duration, an error message is displayed (step 446) and the routine returns to the AWAKE TEST prompt (step 440). If the interval duration is within acceptable bounds the routine continues to link step 448.

FIG. 10 continues illustration of the Enter Monitor Parameter Routine. Link step 448 continues with guiding entry of test intervals during the patient's sleeping interval. Step 450 prompts entry of the patient's normal bed time, which results in the monitor shifting from a typically more frequent waking time schedule to a sleeping period schedule of reduced frequency. The prompt display is "BED TIME= #" and entry of the first digit again results in calling the Parameter Entry Subroutine (step 452). After entry of a parameter of reasonable length the parameter is checked for conformity to the 12 hour clock (step 454), in other words an entry of less than 1300 hours. Where this condition is not met an error condition is indicated (step 456) and the routine is returned to the BED TIME prompt to repeat the sequence. Where the value of the parameter is reasonable the routine continues to military time (24 hour clock) conversion beginning at step 458.

Step 458 is a prompt displaying "PRESS #=AM 1=PM" allowing the user to indicate whether the preceding bed time entry is a AM or a PM entry. Four entries are accepted: a "*" entry (step 460) which results in the routine being aborted to the idle link step 556; a "1" entry (step 462) which results in the time entry of step 450 having 12 hours added to it in step 468 before the routine proceeds to link step 470; and a "#" or "0" entry (step 464), either of which result in the routine skipping the 24 hour conversion step 468 to link step 470. Entry of any other character results in display an entry error condition (step 466) and looping of the routine back to the beginning of AM/PM determination beginning with step 458.

Link step 470 leads the routine into the portion of the routine dedicated to setting the sleeping period test interval. Step 472 prompts the scrolled display of two prompts "SLEEP TEST" and "INTERVAL= MIN#". Entry of the first digit results in calling the Parameter Entry Subroutine (step 447) freezing the display on the latter prompt and display of an integer if entered. At step 476 the proposed parameter is checked for conformity to minimum and maximum durations of 5 and 240 minutes respectively. An out of bounds entry results in display of an entry error message (step 478) and looping of the routine back to step 472. A parameter conforming to the bounds results in the routine proceeding to step 480.

Step 480 of the routine directs display of the prompt "TEST=1, SAVE=2". Three entries are accepted: a "*" results in aborting the routine (step 482) and exiting to the idle routine (step 556); a "1" entry results in the routine exiting to the monitor test routine (step 484) by link step 200; and a "2" entry results in the routine storing the parameters (step 486) to monitor memory (step 490) and display of the message "PARAMETERS SAVED" before the routine is exited to the monitor test routine through link step 200. Entry of any other character results in the routine looping back from test step 486 to step 480, with an intermediate entry error message display (step 488).

Figure 11:
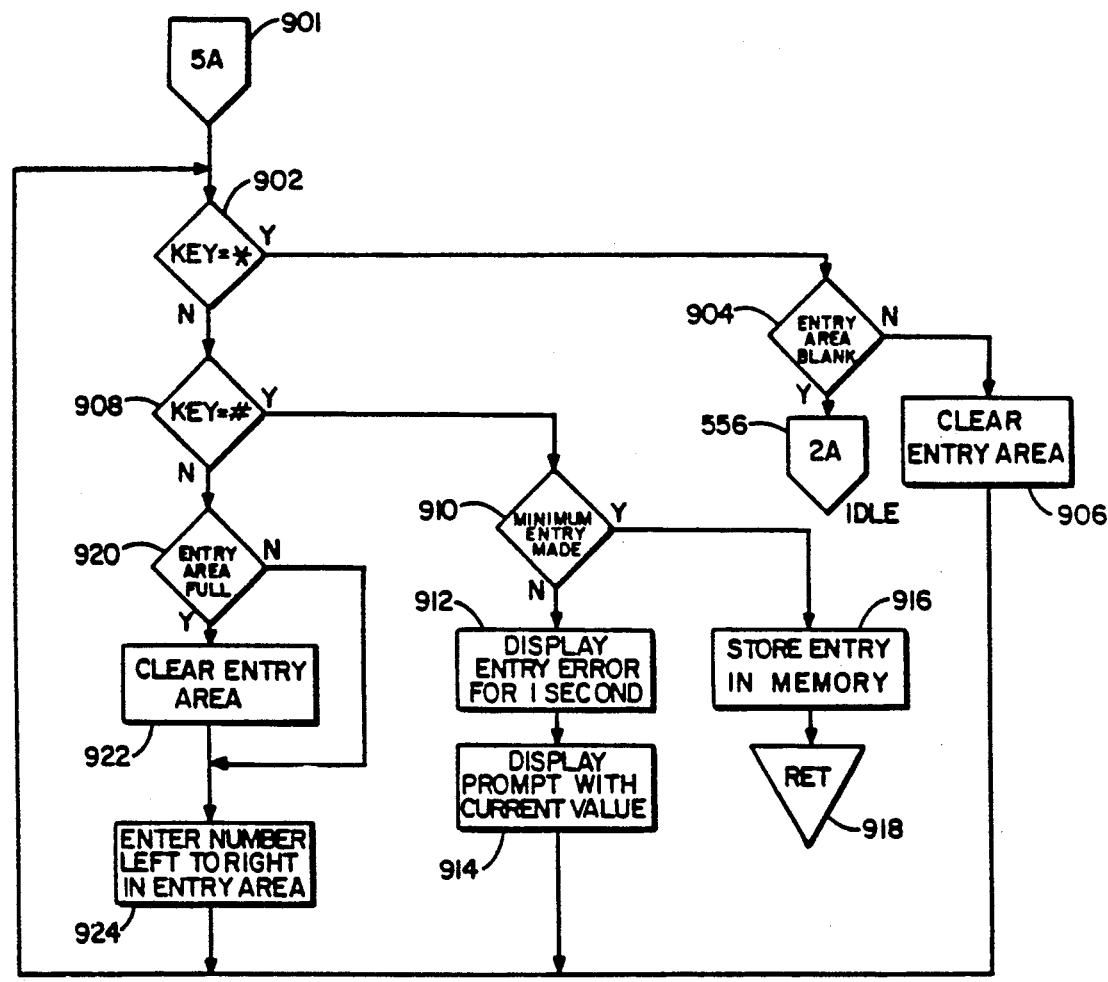
FIG. 11 is a flow chart diagram of a parameter entry subroutine.

FIG. 11 illustrates the Parameter Entry Subroutine, which is called from the principal routines. The Parameter Entry Subroutine determines whether the length of a parameter proposed for entry by a user conforms with the length requirements for that parameter. The various parameters to be entered have differing maximum lengths, the subroutine receiving length information from the size of the parameter entry area in a given parameter entry prompt. As noted in the forgoing discussion of entry of specific parameters, entry to the Parameter Entry Subroutine freezes a selected parameter entry prompt on the display of the control unit at link step 901.

At step 902 keypad 14 is scanned for entry of the clear sign "*". Detection of such an entry branches the program to step 904, resulting in the microprocessor scanning the entry area in memory corresponding to the entry area of the parameter entry prompt. If the parameter entry area is empty, the subroutine and the calling routine are exited and the program returns to the idle loop by link step 556. If entries have been made, or another number such as a default parameter is present in the entry area, the entry area is cleared (step 906) and the program loops back to step 902. At step 908 the routine directs scanning the keypad for entry of the "#" key. The pound key is used by the operator to indicate that the current display in the parameter entry area is to be used as the parameter. Detection of the "#" key branches the routine to step 910 where it is determined whether the number, if any, in the parameter entry area has the requisite minimum number of digits. The entry cannot have too many digits as will be explained below. If the entry has the minimum required number of digits, the parameter is stored to control unit memory (step 916) for evaluation by the routine for conformity to magnitude requirements. The subroutine is exited back to the original routine through link step 918. If the proposed entry is too short, the subroutine branches to step 912, resulting in display of an entry error message for 1 second and thereafter display of the entry parameter prompt with the parameter value previously proposed (step 914). The subroutine then loops back to step 902.

Where a digit is entered by the user, the routine passes from step 902 to step 908 to step 920, which determines whether the entry area is full or not. If the entry area is full, the area is cleared and the new entry is entered into the area (steps 922 and 924). If the entry area is not full, the new digit is entered into the area, each successive digit being introduced from left to right (step 924). From step 924 the subroutine loops back to step 902.

Figure 12A:
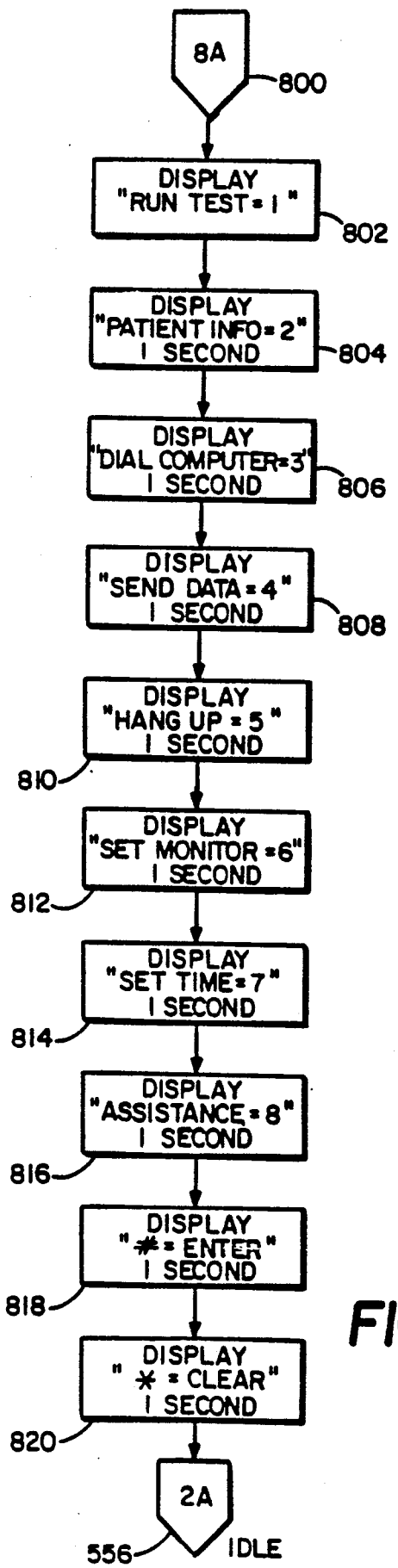
FIG. 12A is a flow chart diagram of the menu assistance routine.

FIG. 12A illustrates the menu loop display routine. The menu loop does not prompt any action on the user's part, but rather simply displays the menu options available from the idle loop. Entry of a "0" in the idle loop results in the menu loop display routine being executed beginning with link step 800. The loop displays the titles of the prompt routines available and the code for entering the corresponding routine. The figure indicates the order of display of the options from the idle loop, each message being displayed for 1 second. Step 802 results in the message "RUN TEST=1", the entry for initiating a test of the patient monitor. In step 804 the message "PATIENT INFO=2" is displayed indicating the routine for transferring results to the central data processing facility. Step 806 displays "DIAL COMPUTER=3" indicating the entry for establishing a data transferral link to the central data processing facility. Step 808 displays the message "SEND DATA=4", indicating that entry of a "4" is used to actually start the transfer of data once a communication link is established. Step 810 indicates display of the message "HANG UP=5", the entry for terminating a data link to the central data processing facility. Step 812 indicates display of the message "SET MONITOR=6", the entry for initiating programming of a patient monitor. Step 814 displays "SET TIME=7" indicating that entry of a "7" starts the reset/power up sequence. Step 816 displays "ASSISTANCE=8", indicating that entry of an 8 runs the menu display. Step 818 displays the message "#= ENTER" and step 820 displays "* = CLEAR", the nonvarying functions of the indicated keys once prompt routines have been entered. The routine reenters the idle loop at the conclusion of the menu routine through step link 556.

Figure 12B:
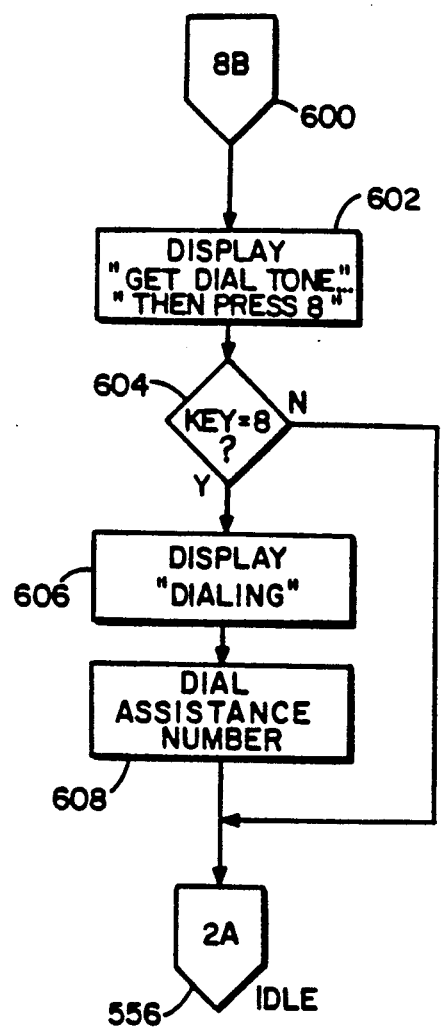
FIG. 12B is a flow chart diagram of the operator assistance subroutine.

FIG. 12B illustrates the assistance routine which is used for establishing a telephone link to a live operator who can advise a system user on problems. Upon entry of an "8" from the idle routine the routine enters the assistance routine through link step 600, prompting the user at step 602 to "GET DIAL TONE . . ." and "THEN PRESS 8 in alternating sequence. Keying any key except the clear key (step 604) results in the control unit displaying a message "DIALING" (step 606) and then dialing an assistance number (step 608), which connects the user to a live operator over the telephone associated with the control unit. After the linkage is broken the routine returns to the idle loop (link step 556). If at step 604 an is detected, the routine skips steps 606 and 608 and immediately returns to the idle loop by link step 556.

Figure 13:
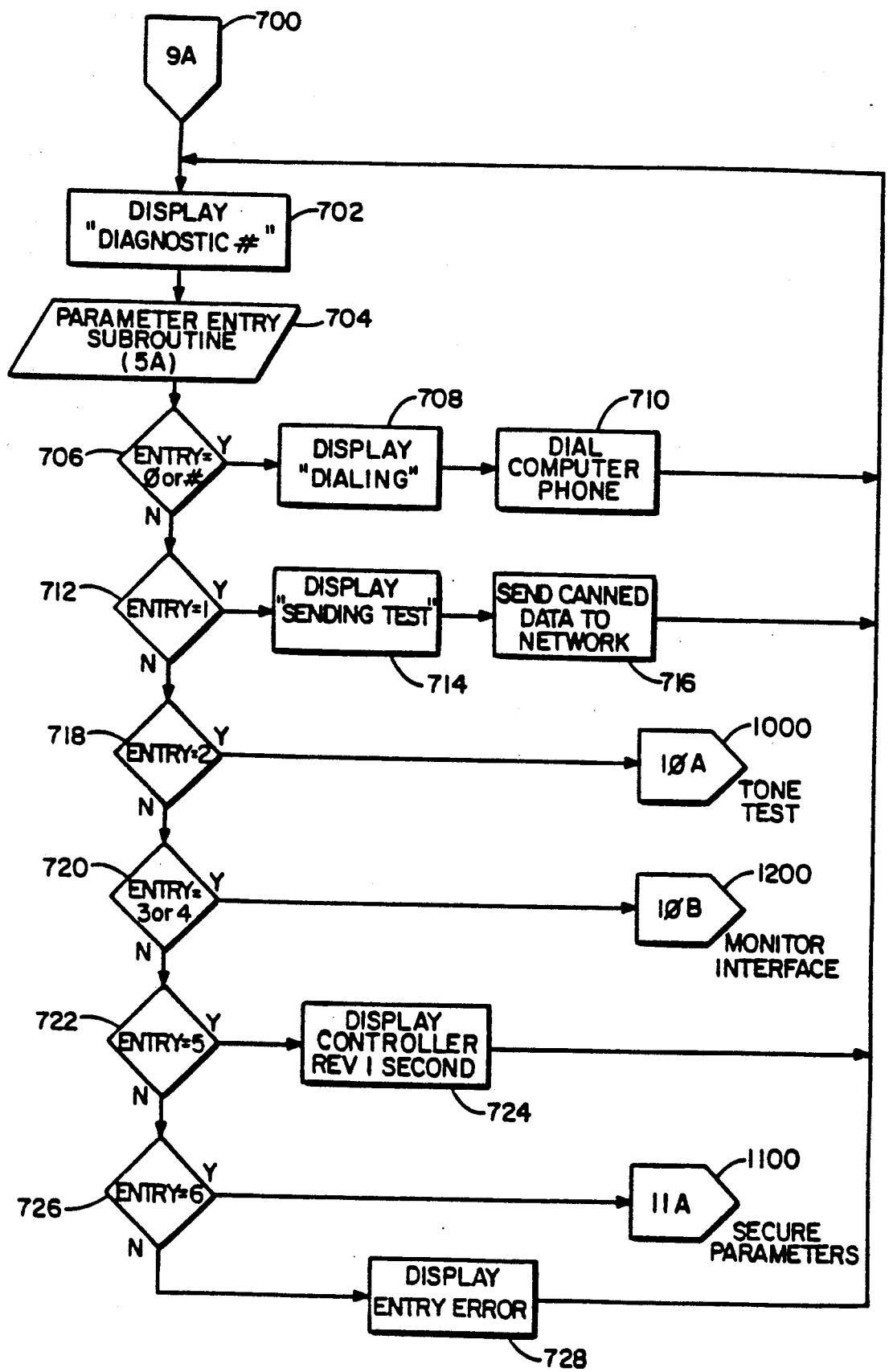
FIG. 13 is a flow chart diagram of a diagnostics routine.
Figure 14:
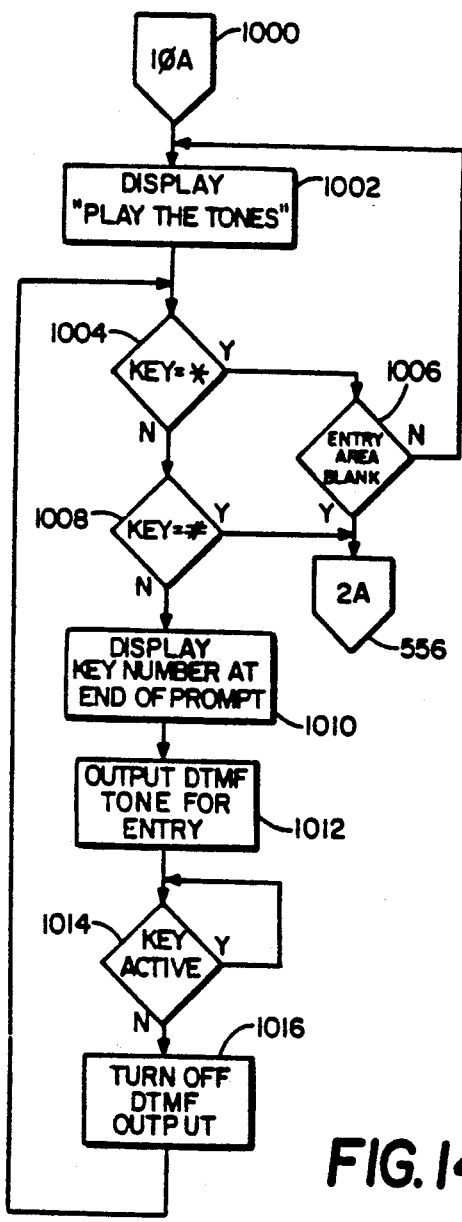
FIG. 14 is a continuation of FIG. 13.
Figure 15:
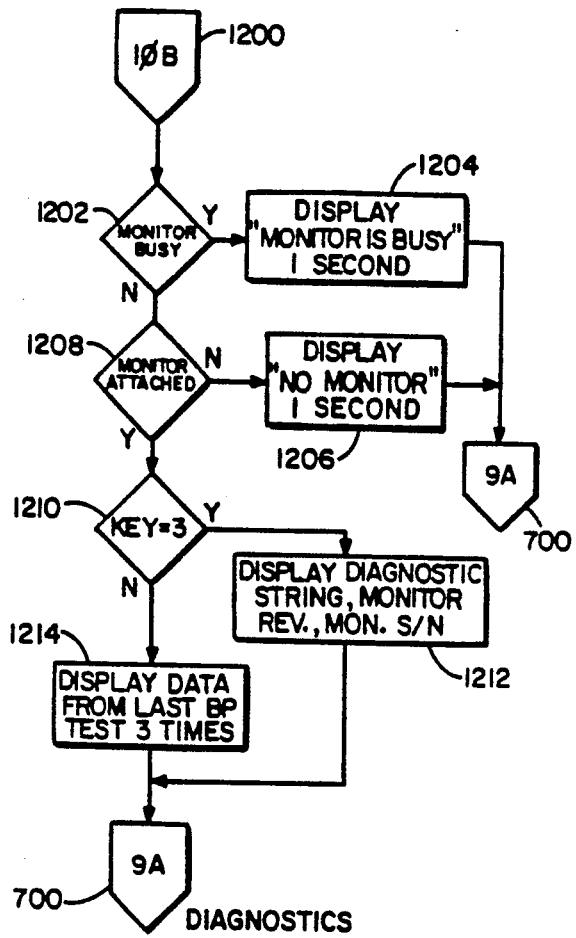
FIG. 15 is a flow chart diagram of a patient monitor diagnostic routine.

The control unit also provides prompted diagnostics for its own electrical circuitry and programming functions as illustrated in FIGS. 13, 14 and 15. The diagnostics routine is entered by entry of a "9" during execution of the idle loop, whereupon the routine enters the diagnostic loop through link step 700. Initiating the diagnostic routines requires entry of a specific test to be performed which is done at step 702, in response to the prompt "DIAGNOSTIC #". The keys "#, 0, 1, 2, 3, 4, 5 and 6" each initiate a test subroutine, and, in the case of "6", also allow reassignment of the control unit.

Entry of a number calls the Parameter Entry Subroutine (step 704) which tests an entry for length. Beginning at step 706 entries are tested for a match to one of the test routines. Step 706 tests for entry of a "0" or "#". Entry of either key initiates a test of connection to the central data processing facility by attempting to establish a data link to the facility. Display of "DIALING" (step 708) and the process of dialing (step 710) take place in response to entry of the noted characters. The routine loops back to step 702 after establishment of the link.

Typically, a command to send test data would now be used in a diagnostic routine. Entry of a "1" at step 702 causes the routine to proceed through steps 704 and 706 to step 712, which detects the "1" and branches the routine over to steps 714 and 716. Steps 714 and 716 send canned data over the network to test the communication link. Specifically, step 714 indicates by the message "SENDING TEST" that the data is being sent and step 716 directs the actual transmission of the canned data stream by DTMF signals. After completion of the transmission the routine loops back to step 702. Entry a "5" directs the routine down through steps 706, 712, 718 and 720 to step 722. Step 722, in response to the "5", branches the routine over to step 724 which is a message step indicating on the control unit display the version of the program stored in the control unit. Again, after the message is displayed for one second, the routine loops back to step 702. Entry of a "7, 8, or 9" results in the program looping back to step 702 through step 728, which displays the message entry error.

Entry of a 2, a 3 or 4, or a 6 initiates one of three different test subroutines. A "2" initiates a tone test through link step 1000. A "3" or "4" initiates a monitor interface test through link step 1200. A "6" initiates a secure parameters subroutine through link step 1100. The last routine is not a diagnostic routine, but rather a security routine through which leased control units can be assigned to a specified location.

The tone test routine is entered through link step 1000, illustrated in FIG. 14, resulting in the subsequent display of the message "PLAY THE TONES" at step 1002. Because data is transferred using the DTMF tones associated with numeric keys on the telephone keypad, this test reproduces those tones for evaluation by a diagnostician. The "*" and "#" keys are reserved for exiting the subroutine, or for clearing a previous entry, as indicated at steps 1004, 1006 and 1008. The subroutine enters step 1004 immediately after step 1002, and scans the keyboard for entry of the "*" sign, which if detected branches the program to step 1006. This results in scanning of the entry area for a character entry. If the entry area is not empty it is cleared, and the subroutine is looped back to step 1002. If the entry area is blank when tested by step 1006, the subroutine is exited back to the idle loop by link step 556. Entry of the "#" sign simply kicks the subroutine out to the idle loop through link step 556 when detected at step 1008.

Entry of a digit key results in the subroutine proceeding through steps 1004 and 1008 to step 1010 which results in the key number being displayed at the end of the "PLAY THE TONES" prompt. At step 1012 the appropriate tone for the key number entered is played over handset 20 (see FIG. 1). Step 1014 indicates that the tone continues to be played until its associated key becomes inactive. At that point the DTMF tone is turned off (step 1016) and the subroutine loops back to step 1004.

FIG. 15 illustrates prompting for initiating testing of a patient monitor. The subroutine is entered from the diagnostic routine through link step 1200, upon which the control unit interrogates the communication port for patient monitors to check on the presence of a monitor and whether the monitor, if present, is busy (steps 1202 and 1208). If either condition fails, i.e. the monitor is busy or no monitor is attached the subroutine is exited to the diagnostic routine by link step 700, displaying the message "MONITOR IS BUSY" (step 1204) or "NO MONITOR" (step 1206), depending upon the condition encountered.

If the conditions are met, in other words an activated, not busy monitor is connected to the control unit, the testing proceeds at step 1210 to determine whether the key used for entry was a "3". If the key was a "3" a diagnostic string is displayed upon interrogation of the monitor (step 1212) indicating the monitor version number and other data. If the key was not a "3", or in other words a "4", the subroutine causes the control unit to display (at step 1214) data from the last blood pressure test executed by the machine three times. After either step 1212 or step 1214 the subroutine escapes to the diagnostic routine by link step 700.

Figure 16:
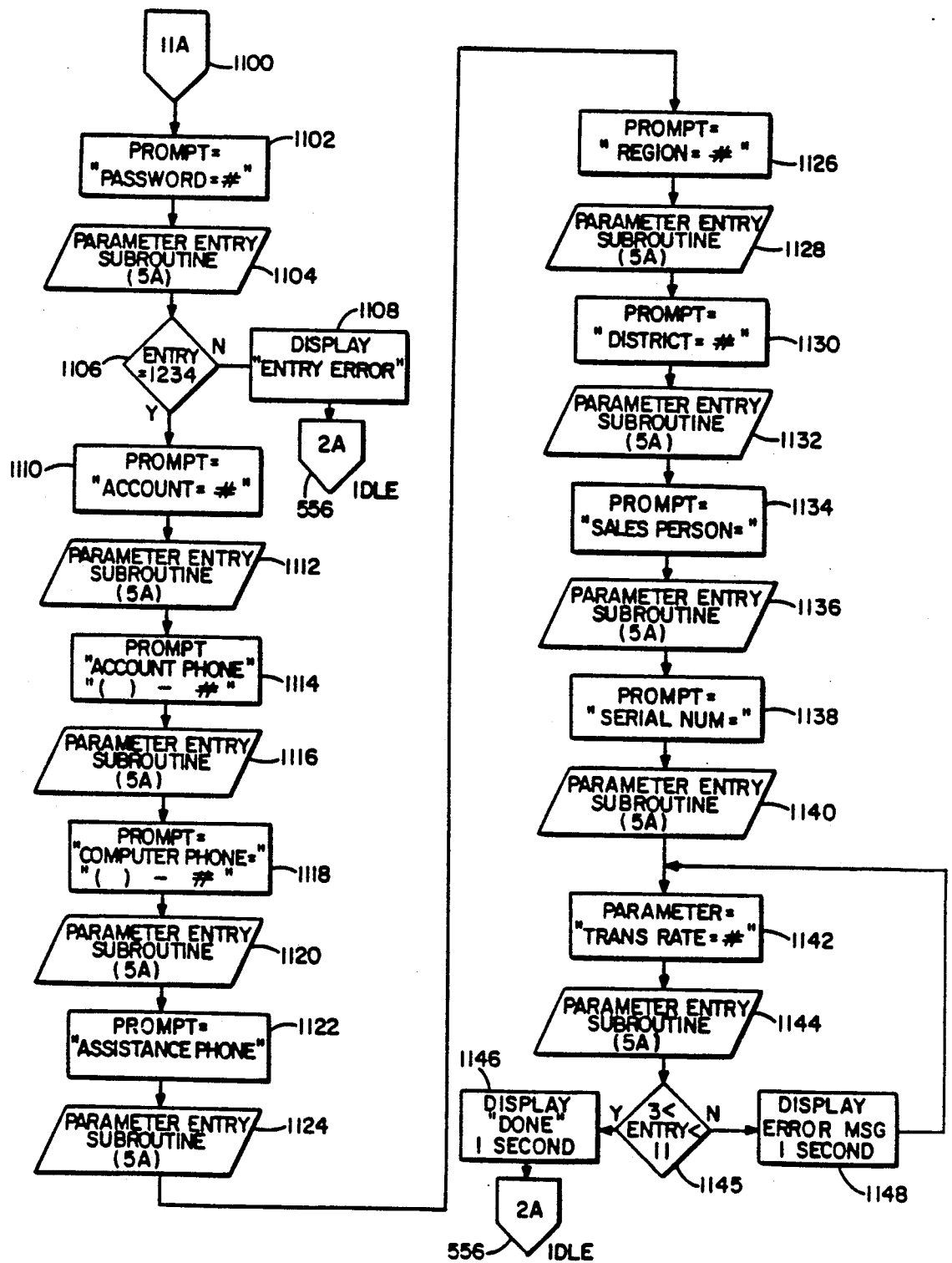
FIG. 16 is flow chart diagram of a secure parameter routine.

FIG. 16 illustrates the prompt routine through which control units are programmed for operation from a particular locale. The routine allows other routines such as a data transfer rate routine to be modified. For example, phone numbers used by the data transfer routine can be modified. Access to the secure parameters subroutine is normally blocked to user personnel by a secret password. Accordingly, after entry to the subroutine through link step 1100 from the diagnostic routine the user is prompted for the control units password by the prompt "PASSWORD= #" (step 1102). Entry of a digit results in the Parameter Entry Subroutine being called at step 1104 which allows the routine to pass to step 1106 only if the entry has the correct number of digits. At step 1106 the entry is checked to see if it conforms to the actual password, herein typically a 4 character string of numbers. If the entry does not conform to the password, the subroutine is exited and the user is returned to the idle loop through link step 556 after display of an entry error message (step 1108).

If the correct password is used the operator is led through a string of prompts allowing selection of phone numbers for channeling calls initiated from the site of the control unit and selection of billing code information. At step 1110 the operator is prompted by "ACCOUNT = #" enter an account number for the contracting user of the control unit. Entry of the account number is monitored by calling the Parameter Entry Subroutine (step 1112). Thereafter the operator is prompted to enter a phone number for the site at which the control unit is being deployed by the alternating prompts "ACCOUNT PHONE" and "( ) — #" (step 1114). Again, entry of a digit results in calling the Parameter Entry Subroutine (step 1116) which freezes the display on the second prompt and displays digits of the number as they are programmed into the control unit. At step 1118 the control unit prompts entry of the phone number for central data processing facility by alternating the prompts "COMPUTER PHONE" and "( ) — #". Step 1120 indicates calling of the Parameter Entry Subroutine. Step 1122 indicates prompting to enter the assistance phone number with the alternating prompts "ASSISTANCE PHONE" and "( ) — #". Again the Parameter Entry Subroutine (step 1124) monitors entry of the phone number.

Optional data can also be entered into control units. Step 1126 allows entry of a code indicating geographic location of the control unit. Step 1126 prompts entry of the code with the prompt "REGION =#". A entry at this step calls the Parameter Entry Subroutine (step 1128). Further specification of the region can be done by entry of a district code at steps 1130 and 1132. The sales representative can be specified by code at steps 1134 and 1136. Steps 1138 and 1140 allow the serial number of the control unit to be read into the unit's own memory. Finally, steps 1142 and 1144 allow the data transfer rate to be entered into control unit memory. This entry made mandatory by step 1145, which specifies selected minimum and maximum data transmission rates and indicates an error condition if the selected rates are not met (step 1148), before the subroutine is looped back to step 1142. If the factors meet the standard of step 1145, the subroutine is exited by step 1146, which indicates "DONE" to show that the routine is being exited and returns execution of the routine to the idle loop by link step 556.

Although the present invention has been described with reference to preferred embodiments, workers skilled in the art will recognize that changes may be made in form and detail without departing from the spirit and scope of the invention.

What is claimed is:

1. In a user interactive data entry and data downloading system including a control unit having a stored program microcomputer, a prompt display and a 12-character telephone keypad, and a communication link to an ambulatory patient monitor, the ambulatory patient monitor including a stored program microcomputer, a method for directing user selection of blood pressure test parameters for transfer to the ambulatory patient monitor; the method comprising the steps of:
   initially entering an idle routine from which any one of a plurality of menu items can be entered by selection of a predetermined key of the keypad, the menu items including a subroutine for assembling a set of blood pressure test parameters;
   displaying on the prompt display indication of execution of the idle routine;
   monitoring the keypad for selection of a key;
   entering a subroutine upon selection of a key associated with the subroutine;
   displaying on the prompt display indication of selection of the subroutine;
   the step of displaying indication of entry of a subroutine including upon entry of the subroutine for assembling blood pressure test parameters, directing, through further visual prompts on the prompt display, selection by the user of blood pressure test parameters through the keypad to establish a blood pressure test regimen;
   determining the reasonableness of the selected blood pressure test parameters upon selection;
   rejecting a selected blood pressure test parameter if unreasonable and directing, through visual prompts, selection of a new blood pressure test parameter;
   transferring the selected blood pressure test parameters to the ambulatory patient unit after completion of the set of blood pressure test parameters; and
   exiting the assembly subroutine and returning to the idle state after completing transfer of the blood pressure test parameters to the ambulatory patient unit.

2. The method of claim 1 wherein the menu items further include a subroutine for testing the operational condition of an ambulatory patient monitor, the method further comprising the steps of:
   entering the operational condition testing subroutine upon selection of a designated key;
   testing the operational condition of a ambulatory patient monitor and displaying indication both of testing and the result of the test; and
   returning to the idle state after testing the ambulatory patient monitor.

3. The method of claim 1 wherein the user interactive data entry and downloading system further includes a telephone set, the control unit being connected between the telephone head set and the telephone base unit permitting data signals to be transmitted from the control unit on voice circuits established through the base unit, a telephone communication system and a data processing facility, the menu further including a data downloading and communication subroutine, the method including the further steps of:
   entering the data downloading and communication subroutine upon selection of a designated key;
   prompting the user through signals on the prompt display to select the appropriate keys to establish a voice circuit link between the control unit through the telephone set to the data processing facility;

the central data processing facility providing audio prompts over the telephone handset to the user to initiate transfer of data from the ambulatory patient monitor to the control unit by directing selection by the user of appropriate keys on the keypad;

transmitting the data to the data processing facility in response to selection of the keys;

the central data processing facility providing further audio prompts directing the user to disconnect the telephone link after completion of transmission; and exiting the subroutine and returning execution to the idle state.

4. The method of claim 3, wherein the menu for the controller of the data entry and downloading system further includes a modification subroutine the data downloading and communication subroutine, the method further comprising the steps of:

entering the modification subroutine from the idle state upon selection of a designated key; prompting entry of parameters for modifying the data downloading and communication subroutine;

directing the user to adjust each modifiable parameter or accept a default value for the parameter of the data transfer routine; and returning execution to the idle state after execution of the modification routine.

* * * * *